Patent Number: 4,859,456
… Date of Patent: Aug. 22, 1989

[54] HAIR RINSE CONDITIONERS WITH SUPERIOR DRY HAIR FEEL AND HIGH HAIR LUSTER

[75] Inventor: Frank W. Marschner, Whitehouse Station, N.J.

[73] Assignee: Colgate-Palmolive Company, New York, N.Y.

[21] Appl. No.: 122,616

[22] Filed: Nov. 19, 1987

Related U.S. Application Data

[63] Continuation of Ser. No. 812,229, Dec. 23, 1985, abandoned.

[51] Int. Cl.$^4$ .......................... A61K 7/06; A61K 7/08; A61K 9/12
[52] U.S. Cl. ........................................ 424/47; 424/70; 514/944
[58] Field of Search .................................... 424/47, 70

[56]  References Cited

U.S. PATENT DOCUMENTS

| | | | |
|---|---|---|---|
| 3,144,391 | 8/1964 | Goff | 424/71 |
| 3,155,591 | 11/1964 | Hilfer | 424/70 |
| 3,694,141 | 9/1972 | Kalopissis et al. | 424/71 |
| 3,766,267 | 10/1973 | Zak et al. | 514/873 |
| 3,855,290 | 12/1974 | Zak et al. | 424/70 |
| 3,876,760 | 4/1975 | Nersesian | 514/941 |
| 3,998,761 | 12/1976 | Gary et al. | 424/70 |
| 4,035,326 | 7/1977 | Meyer-Stoll et al. | 424/47 |
| 4,220,168 | 9/1980 | Newell | 424/70 |
| 4,374,125 | 2/1983 | Newell | 514/773 |
| 4,421,740 | 12/1983 | Burton | 424/70 |
| 4,517,175 | 5/1985 | Iwabuchi et al. | 424/47 |
| 4,530,830 | 7/1985 | McKaba et al. | 424/71 |

FOREIGN PATENT DOCUMENTS 1532585 11/1978 Fed. Rep. of Germany ........ 424/70

OTHER PUBLICATIONS

Sagarin, *Cosmetics Science & Technology*, p. 405 (1957).

Primary Examiner—Dale R. Ore
Attorney, Agent, or Firm—Richard J. Ancel; M. E. Delsignore; R. C. Sullivan

[57]  ABSTRACT

A stable hair rinse conditioning composition to provide superior dry feel and high luster properties, comprising about 0.5–15% by weight of a polyvinyl pyrrolidone/vinyl acetate copolymer, about 0.1–10% by weight of at least one hydrophilic cationic quaternary ammonium compound, and a water-soluble nonionic cellulose polymer such as hydroxyethyl cellulose, hydroxymethylpropyl cellulose, etc., in an aqueous vehicle.

12 Claims, No Drawings

HAIR RINSE CONDITIONERS WITH SUPERIOR DRY HAIR FEEL AND HIGH HAIR LUSTER

This is a continuation of co-pending application Ser. No. 812,229 filed on Dec. 23, 1985, now abandoned.

FIELD OF INVENTION

The present invention relates to novel hair rinse conditioning compositions, which may be clear or opaque, capable of providing superior dry feel and high luster properties to hair treated therewith, comprising a ternary mixture of polyvinyl pyrrolidone/vinyl acetate (PVP/VA) copolymer, at least one hydrophilic cationic quaternary ammonium compound and a water soluble nonionic cellulose polymer in an aqueous vehicle. The use of this ternary mixture is essential in order to obtain the superior dry feel and high luster hair properties. Also, this mixture is readily and completely removable from the hair by simply shampooing; and does not cause an undesirable build-up of conditioner on the hair.

BACKGROUND AND PRIOR ART

Conventional rinse conditioners comprise cationic-fatty alcohol emulsion systems which tend to oil and grease the hair. The cationic quaternary compounds may have a hydrophobic group or groups such as lauryl, cetyl, stearyl or benzyl attached to the nitrogen atom or may have a less hydrophobic group such as a polyoxypropylene amido alkyl radical of 3 to 60 propylene oxide groups attached to the nitrogen atom as shown in U.S. Pat. No. 3,155,591. These hair substantive cationics are used to emulsify oils or fatty substances such as fatty alcohols, amides or glycols to enhance the wet and dry combing properties of the cationic. Unfortunately, they provide conditioning of an oily or fatty nature that leaves a dulling effect on the hair.

The prior art also discloses other hair conditioning compositions containing conventional hydrophobic quaternary ammonium compounds containing a higher alkyl or alkenyl group of more than eight carbon atoms, usually 16–18 carbon atoms, together with resins such as PVP/VA copolymers in hair setting compositions. More specifically, U.S. Pat. No. 3,144,391 shows hair setting compositions containing water insoluble copolymers of vinyl pyrrolidone with vinyl esters of fatty acids such as a copolymer of vinyl acetate and vinyl pyrrolidone (40:60 to 85:15) and a minor proportion of a cationic surfactant containing a hydrocarbon radical of at least 8 carbon atoms and ethyl alcohol. U.S. Pat. No. 3,694,141, too, discloses a method of hair conditioning by applying an aqueous setting solution comprising a disulfide compound containing a nitrogen atom, a PVP/VA copolymer and a minor proportion of a quaternary ammonium compound such as trimethyl cetyl ammonium bromide (column 6 lines 15–30). Similarly, U.S. Pat. No. 4,348,383 discloses hair setting lacquers or lotions comprising dithioether compounds for reducing the oily appearance of the hair in combination with a cosmetic resin such as PVP/VA copolymers (column 3 lines 53–54) and quaternary ammonium compounds (column 4 lines 7 and 52–54) in an aqueous, alcoholic, or hydroalcoholic solution. However, this group of patents relates primarily to hair setting solutions containing the PVP/VA copolymer as the film-forming agent, not to hair rinse conditioners which give the hair superior dry feel and high luster properties.

The prior art also discloses water-soluble quaternary ammonium compounds as a skin substantive emollient in cosmetic products, e.g., hair styling gels shown in U.S. Pat. Nos. 3,766,267 and 3,855,290 which further include a carboxylated vinyl polymer. On the other hand, said water-soluble quaternary ammonium compounds have been used as a conditioning agent in hair rinses containing a lubricant such as a higher fatty alcohol as shown in U.S. Pat. No. 3,155,591. But, no PVP/VA copolymer or other quaternary compound is disclosed in this group of compositions.

U.S. Pat. Nos. 4,220,168 and 4,374,125 disclose, respectively, a moisture control hair spray composition containing PVP/VA copolymers as an optional ingredient and a moisture stabilizing conditioner containing a quaternary ammonium salt conditioner as an optional ingredient.

However, none of the foregoing patents discloses a hair conditioning composition having dry feel and high hair luster properties comprising the ternary mixture of a PVP/VA copolymer, one or more hydrophilic cationic quaternary ammonium compounds and a water soluble nonionic cellulose polymer in an aqueous medium wherein said quaternary compound is present in the prescribed proportion to the PVP/VA copolymer.

SUMMARY OF THE INVENTION

It has been found that a hair rinse conditioning composition comprising a ternary mixture of a PVP/VA copolymer, a hydrophilic quaternary ammonium compound(s) which is free of alkyl radicals of more than 8 carbon atoms and a water soluble nonionic cellulose polymer in an aqueous medium provides a stable composition which imparts superior dry feel and hair luster properties as well as very good body and dry hair manageability to hair treated therewith.

Accordingly, a primary object of the present invention is to provide a hair rinse conditioner which imparts superior dry feel and high luster properties to the hair comprising a ternary mixture of a PVP/VA copolymer, at least one hydrophilic quaternary compound having water solubility which are free of hydrophobic alkyl or alkenyl radicals of more than eight carbon atoms in the molecule and a water soluble nonionic cellulose polymer in an aqueous medium.

Another object of present invention is to provide a hair rinse conditioner which provides good body and dry hair manageability to the hair treated with said conditioner.

Still another object of this invention is to provide an aqueous hair rinse conditioner having minimal build-up effects on the hair.

Still another object of this invention is to provide a hair rinse conditioner which is readily removable from the hair by simply shampooing.

Additional objects, advantages and novel features of the invention will be set forth in part in the description which follows, and in part will become apparent to those skilled in the art upon examination of the following description or may be learned by practice of the invention. Also, the objects and advantages of the invention may be realized and and attained by means of the instrumentalities and combinations particularly pointed out in the appended claims.

To achieve the foregoing and other objects and in accordance with the present invention, as embodied and broadly described herein, the novel hair rinse conditioning composition of this invention comprises a ternary mixture of a polyvinyl pyrrolidone/vinyl acetate (PVP/PA) copolymer, at least one hydrophilic cationic quaternary compound which is free of alkyl or alkenyl radicals containing at least eight carbon atoms in the molecule and a water soluble nonionic cellulose polymer in an aqueous medium. The aqueous medium constitutes about 71% to 99.3%, preferably 80% to 98.3%, most preferably 90% to 97.7% by weight of the composition.

More specifically, the present invention relates to a hair conditioning composition which provides the hair treated therewith with superior dry feel and high luster properties, containing as the essential conditioning agents, a ternary mixture of about 0.5-15 by weight of a PVP/VA copolymer, about 0.1%-10% by weight of at least one cationic quaternary compound with a hydrophilic group attached to the nitrogen atom, and about 0.1-4% by weight of a water soluble nonionic cellulose polymer in 71-99.3% by weight of an aqueous vehicle.

The performance criteria of a good hair conditioning rinse is: disperses well throughout the hair upon application; provides good ease of wet combing, i.e., detangles the hair without damaging it; provides good ease of dry combing with good hair manageability; and maintains good hair shine without an oily feel. Typically, clean hair is shiny and hair treated with rinse conditioners is usually dull in appearance.

DETAILED DESCRIPTION OF THE INVENTION

It has been found that more desirable rinse conditioners can be made by using polyvinylpyrrolidone/vinyl acetate (PVP/VA) copolymers in place of the fatty materials conventionally used. Such conditioners impart a dry feel, good body and improved shine properties to the hair. Further, it has been found that superior dry feel/high hair luster rinse conditioners can be made by employing such polyvinylpyrrolidone/vinyl acetate copolymers in combination with a quaternary ammonium compound which has hydrophilic properties, i.e., a compound which is wholly or partly soluble in water and does not contain a hydrophobic alkyl or alkenyl radical of more than eight carbon atoms in the molecule. This improved rinse conditioner imparts good wet combing, superior hair luster, good body and very good dry hair manageability to hair treated therewith. It has also been found that the addition of the more hydrophilic cationic compound enhances the hair shine properties of PVP/VA copolymer rinse conditioners even when a usual hydrophobic type cationic compound such as stearyl dimethyl benzyl ammonium chloride or di-hydrogenated tallow dimethyl ammonium chloride is present, too. Furthermore, the presence of a water soluble nonionic cellulose polymer further enhances the conditioning properties of the hair rinse-conditioner. It is believed that the coaction of this ternary mixture of ingredients is responsible for the superior and unexpected conditioning effects, including the substantial absence of conditioner build-up on the hair. The three essential ingredients are completely compatible.

The PVP/VA copolymer, which is one of the essential components of present invention, is a substantially water insoluble film forming material which has been used in the prior art in hair sprays, liquid or foam hair setting compositions and the like. Suitable PVP/VA copolymers are obtainable from the GAF Corporation in the form of a 50% A.I. (active ingredient) clear liquid solution in either ethanol or isopropanol at room temperature, with the weight ratio of PVP/VA varying from 70:30 to 30:70. For example, PVP/VA E-735 is a 50% (AI) solution in ethanol of PVP/VA in the weight ratio of 70:30; PVP/VA E-335 is a 50% (AI) solution in ethanol of PVP/VA in the weight ratio of 30:70 and PVP/VA I-735 is a 50% (AI) solution in isopropanol of PVP/VA in the weight ratio of 70:30. The alcohol solutions of the PVP/VA copolymers exhibit water tolerance, thereby enabling their use in aqueous systems such as aqueous conditioning compositions. For example, the water tolerance of PVP/VA copolymers of the E-Series, expressed in parts of water added to 100 parts of a 25% copolymer solution in anhydrous ethanol until the appearance of a slight haze, is as follows:

| Polymer | Water Tolerance |
| --- | --- |
| PVP/VA E-735 | 540 parts water |
| PVP/VA E-535 | 175 parts water |
| PVP/VA E-335 | 120 parts water |

In use, a clear film of PVP/VA copolymer is deposited on the hair treated with compositions containing such polymers to provide hair with a high luster. The PVP/VA copolymer is used in amounts of about 0.5% to 15%, preferably 0.9% to 10% and most preferably 1.35% to 3% by weight of the composition.

Another essential ingredient in the novel hair rinse composition is a cationic quaternary ammonium compound, which exhibits at least partial solubility in water. Such compounds do not contain a hydrophobic alkyl or alkenyl group of at least eight carbon atoms in their molecular structure like the traditional conditioning quaternary ammonium compounds such as cetyl or stearyl dimethylbenzyl ammonium chloride, but contain a polyoxyalkylene radical of at least nine carbon atoms in their molecular structure. Because of this difference, these compounds exhibit solubility in water varying from complete water solubility for compounds containing a relatively low number of $C_3$-$C_4$ alkylene oxide groups, e.g., eight propylene oxide groups, to partial solubility in water for compounds containing a higher number of said alkylene oxide groups, e.g., twenty-five or forty-one propylene oxide groups. These ingredients exhibit cationic surface functionality in both oil and water, with the lipophilic tendency being proportional to the amount of polyether structure comprising the individual compound's molecular weight. A high order of antistatic efficiency is due to the combined effects of their cationic activity and the hygroscopicity of their polyether structures.

Suitable compounds generally correspond to the following formula:

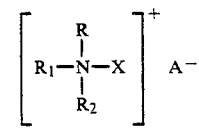

wherein R and $R_1$ each is an alkyl radical containing 1-3, preferably 1-2, carbon atoms; $R_2$ is a polyoxyalkylene radical represented by either $[CH_2CH(R_4)O]_nH$ or alkylene $O[CH_2CH(R_4)O]_nH$ where $R_4$ is an alkyl radical of 1-2 carbon atoms, preferably methyl, n is 3 to 60, preferably 9 to 41, and alkylene contains not more than three carbon atoms; X is a lower alkyl or alkenyl radical containing 1 to 4 carbon atoms or is an alkaryl radical containing from 7 to 9 carbon atoms; and A is an anion selected from the group consisting of chlorine, bromine, hydroxy, sulfate, metho- or ethosulfate, nitrate, phosphate, acetate, formate and sulfonate, preferably chlorine or bromine. Particularly preferred compounds are methyl, diethyl, polyoxypropylene (8–41) quaternary ammonium chlorides. These preferred compounds may be purchased from Witco Chemical Company under the tradenames Emcol CC9 (quaternium 6) containing 9 moles of propylene oxide; Emcol CC-36 (quaternium 20) containing about 25 moles of propylene oxide; and Emcol CC-42 (quaternium 21) containing 41 moles of propylene oxide.

The method of making these quaternary ammonium compounds is described in U.S. Pat. Nos. 3,141,905, 3,155,591 and 3,123,641 and the disclosures of these patents are hereby incorporated by reference in this specification.

Because of the substantivity to the hair of the foregoing quaternary ammonium compounds, said compounds appear to coact with the PVP/VA film forming ingredient to yield treated hair with an adherent lustrous film that can be readily removed by washing with a shampoo. In addition, these ingredients are essentially non-irritating and are compatible with anionic and nonionic surfactants as well as with phenolic germicides. The cationic polyoxyalkylene quaternary ammonium compounds constitute about 0.1% to 10%, preferably 0.45% to 8%, most preferably 1.35% to 3%, by weight of the hair conditioning composition. Furthermore, the weight ratio of these cationic polyoxyalkylene quaternary ammonium compounds to the PVP/VA polymer ingredient should be controlled in the range of 1:5 to 20:1, preferably from 1:3 to 2:1.

The third essential ingredient in the hair conditioning compositions is a water-soluble, nonionic, cellulose polymer which functions both as a thickening agent and as a conditioning agent. Suitable cellulosic polymers are selected from the group consisting of hydroxyethyl cellulose and hydroxypropyl methyl cellulose, with hydroxyethyl cellulose being preferred. Hydroxyethyl cellulose is the product of reaction between an alkali cellulose and ethylene oxide, and such products are available in a number of viscosity grades. Viscosity is primarily dependent upon the viscosity of the cellulose used in the reaction. The degree of substitution of hydroxyethyl groups per glucose unit is 1.4–1.5 and these hydroxyethyl celluloses have an average molecular weight range from about 80,000 to about 900,000. A particularly preferred hydroxyethyl cellulose is available under the tradename Natrosol 250 HR from Hercules, Inc. Water-soluble hydroxypropyl methyl cellulose has a methoxyl content between about 25% and about 32% by weight and a hydroxypropyl content between about 2% and 10%, preferably 2% to 7%, by weight. Again, the chain length of the cellulose used in the reaction can be controlled to provide a molecular weight which yields a viscosity for a 2% solution in water in the range of 10 cps and 5000 cps, preferably 50 cps to 4000 cps.

These cellulose polymers provide stability to the composition upon aging by viscosity control. The composition retains its viscosity without thinning out or thickening. In addition to controlling the viscosity of the aqueous hair rinse, the cellulose polymer contributes to its conditioning properties. It appears that hydrogen bonding occurs between the water soluble nonionic cellulose polymer and the cationic quaternary compound, resulting in additional conditioning benefits to the hair rinse. This unexpected dual function and coaction with the other two essential conditioning ingredients provides a uniquely superior hair rinse product. The cellulose polymer content constitutes about 0.1–4%, preferably 0.2% to 2%, most preferably 0.25% to 1.2%, by weight of the conditioning hair rinse composition.

The final essential ingredient in the conditioning hair rinse compositions is an aqueous medium which is primarily water. Since the PVP/VA polymer is usually supplied as a solution in ethanol or isopropanol, the aqueous medium usually contains a minor amount of a $C_2$–$C_3$ alkanol. Furthermore, if desired, additional amounts of $C_2$–$C_3$ alkanol may be added to the composition, particularly where the composition is sold in the form of a "mousse." The proportion of the aqueous medium is in the range of 71% to 99.3%, preferably 80% to 98.3%, most preferably 90% to 97.7%, by weight of the hair rinse composition. Usually, the $C_2$–$C_3$ alkanol will be a minor proportion of the aqueous medium, ranging from 2% to 25% by weight of the hair rinse composition, with the higher amounts of such alkanol being present in the "mousse" compositions.

An optionally desirable component in present hair conditioning composition is a foaming cationic surfactant which functions as a dispersant and contributes to the conditioning properties of the final product. This cationic surfactant is a hydroxylated quaternary ammonium compound containing polyethoxy radicals, a gluconamidopropyl radical, or a hydroxylated gluconamido $C_1$–$C_3$ alkyl radical attached to the nitrogen atom, at a concentration of 0.1% to 8%, preferably 0.5% to 4%, by weight.

A typical hydroxylated cationic quaternary ammonium compound containing a gluconamidopropyl radical is Quaternium 22 ($\gamma$-gluconamidopropyl dimethyl 2-hydroxyethyl ammonium chloride). Quaternium 22 is a water soluble gluconamidopropyl quaternary salt which can be obtained from the Van Dyke Company under the tradename Ceraphyl 60 in the form of a clear yellow to light amber liquid containing 58%–62% by weight of said salt in water, having a pH of 4–5 and a specific gravity at 25° C. of 1.17–1.21. The method of preparing this compound is fully described in U.S. Pat. No. 3,766,267, the subject matter thereof being incorporated by reference herein.

A typical hydroxylated quaternary compound containing polyethoxy radicals is Quaternium 36 (stearyl pentaethoxy ammonium chloride) which may be obtained from the Hoechst Company under the tradename Genamin KS-5 in the form of a clear yellow liquid containing 20%–22% by weight of said quaternary salt in water. The pH of Genamin KS-5 is 6.5±0.5. Quaternium 36 has the following chemical formula:

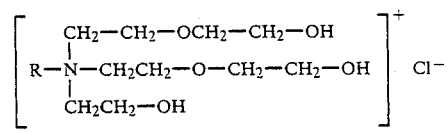

wherein R is primarily $C_{18}$.

Another hydroxylated quaternary ammonium compound containing polyethoxy radicals is alkylpolyethoxy ammonium lactate having the following formula:

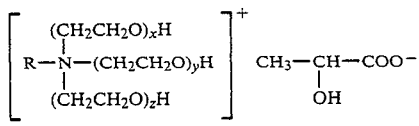

wherein R is primarily $C_{18}$ and the sum of $x+y+z$ is approximately 5. This alkyl pentaethoxy ammonium lactate also is obtainable from the Hoechst Company as a clear liquid in the form of a water/ethylene glycol solution containing 30% of said quaternary compound under the tradename of Genamin KSL.

The hair conditioning compositions in accordance with this invention may be in the form of a clear or opaque pourable liquid, gel or liquid under pressure for use either as a hair rinse after shampooing or as a hair conditioning-styling mousse. The viscosity of the final product may range from at least 50 centipoises to up to 20,000 centipoises and such product may be in the form of a liquid, a viscous lotion or a cream. The hair conditioning product in the form of a gel may be packaged in and extruded from a squeeze tube or any suitable container by applying pressure. Thus, the product may be in the form of a liquid under pressure packaged in an aerosol container containing propellant, a package that is particularly useful for hair styling mousses. In lieu of the aerosol container, the conditioning product also may be packaged in a squeeze spray container.

The pH of the hair conditioner of present invention is acidic and ranges from about 3-6, preferably about 4-5.

The hair conditioning compositions of this invention also may contain conventional additional components such as coloring agents, perfumes, preservatives such as formaldehyde (formalin), brighteners such as Uvinul, cationic hydrophobic quaternary ammonium compounds, and other polymers such as copolymers of polydimethylsiloxane and a polyoxyalkylene ether. The total weight of these optional additives usually does not exceed 5% by weight of the composition and preferably does not exceed 2% by weight of the composition.

The present hair conditioning compositions are readily made by mixing the ingredients in the prescribed manner. For example, a preferred method of preparing the present compositions comprises the steps of forming a thick uniform dispersion of hydroxyethyl cellulose by mixing the hydroxyethyl cellulose in cold water, heating the dispersion to about 60° C. until thick and thereafter cooling to 49° C.; sequentially admixing the quaternary ammonium compound(s) (Quaternium 21, Quaternium 22 and Quaternium 36) and the PVP/VA copolymer with said dispersion; cooling the mixture to 38° C.; adding thereto the colorant, perfume, formalin and other optional additives with agitation; and cooling the resultant mixture to room temperature (24° C.) thereby forming an opaque or clear product. Instead of sequentially adding the cationic quaternary compound(s) and the PVP/VA copolymer, said compounds may be premixed and added as a premix to the thick aqueous hydroxyethyl cellulose dispersion.

These hair conditioner products have unexpected superior properties due to the coaction of the specific ternary combination of PVP/VA copolymer, the cationic quaternary compound having a polyoxyalkylene group attached to the nitrogen atom and the nonionic water soluble cellulose polymer. The novel hair conditioner compositions provide a dry feel, very good body and superior high luster properties to the hair treated therewith and eliminate the dulling of clean hair resulting from the use of conventional hair conditioners. In addition, the inventive conditioners exhibit complete wash-off with shampoos, whereas conventional conditioning hair rinses or hair mousses are retained, thereby resulting in an undesirable build-up of conditioner on the hair. Consequently, continual usage of the conventional hair conditioners dulls the hair. Present products have eliminated this problem. Additional conditioning benefits imparted to the hair include very good wet and dry combing, very good manageability and good anti-static properties.

The following examples are merely illustrative of the invention, but it is understood that the invention is not limited thereto. All amounts of various ingredients in the examples, as well as elsewhere in the specification, are by weight unless otherwise specified.

EXAMPLE 1

| Opaque Rinse Conditioner | |
|---|---|
| Ingredient | % by wt. |
| Water | 87.3 |
| Hydroxyethyl cellulose[1] | 1.2 |
| Quaternium 21[2] | 4.5 |
| Quaternium 22[3] | 1.5 |
| PVP/VA (70/30) copolymer[4] | 2.5 |
| Ethanol | 2.5 |
| D C Yellow #10 (1%) | 0.2 |
| Perfume | 0.2 |
| Formalin | 0.1 |
| | 100.0 |

[1]Purchased from Hercules Inc. under the name Natrosol 250 HR
[2]Polyoxypropylene (40) methyl diethyl ammonium chloride (98% AI) and water (2%) purchased from Witco Chemical Corporation as Emcol CC-42.
[3]Gluconamidopropyl, dimethyl, 2-hydroxyethly ammonium chloride (58–62% AI) and 38–42% water purchased from Van Dyk and Company as Ceraphyl 60
[4]Polyvinylpyrrolidone/vinyl acetate copolymer 70/30 purchased from GAF Corporation under the name PVP/VA E-735 as a 50% by weight solution of polymer in ethanol The hydroxyethyl cellulose is dispersed in cold water with mixing and the mixture is heated to 60° C.–66° C. until thick and uniform and thereafter cooled to 49° C. Quaternium 21, Quaternium 22 and PVP/VA E-735 are sequentially added to the cellulose dispersion with agitation and mixed until homogeneous. The mixture is cooled to 38° C. and the color, perfume and formalin are admixed therewith. The product becomes opaque upon cooling to 24° C. to 29° C.

When applied to the hair, this product distributes well throughout the hair and rinses out well. Wet and dry combing are very good and the hair maintains good shine even after 1 hr. of blowdrying. Manageability is very good and the hair feels dry, has good body and no static.

This product aged satisfactorily for 13 weeks under accelerated aging conditions at temperatures of −18° C., 4° C., 25° C., 38° C. and 49° C.

Unlike current (prior art) rinse conditioners containing $C_{12}$–$C_{18}$ mono-alkyl and dialkyl quaternary ammonium salts that build-up on the hair with multiple shampoo-rinse conditioner treatments, this product washes out of the hair with shampooing which is a desirable attribute. In addition, it appears from practical use testing that the degree of conditioning can be controlled with this product by varying the rinsing time. Short rinse periods provide maximum conditioning, and long rinse periods provide less conditioning effects. For maximum conditioning properties this product can be applied directly to the hair without rinsing. Such use suggests that this conditioner has application as a hair mousse.

EXAMPLE 2

| Rinse Conditioner | |
|---|---|
| Ingredient | % by wt. |
| Water | 84.2 |
| Hydroxyethyl cellulose[1] | 1.0 |
| Quaternium 21 | 3.5 |
| Ethanol | 7.0 |
| PVP/VA (50/50) copolymer[5] | 3.0 |
| Perfume | 0.2 |
| Copolymer of polydimethyl siloxane and poloxyalkylene ether 6 | 1.0 |
| Formalin | 0.1 |
| | 100.0 |

[5]Polyvinylpyrrolidone/vinyl acetate copolymer (50/50) purchased from GAF corporation under the name PVP/VA E-535 as a 50% weight solution of polymer in ethanol.
[6]Purchased from General Electric Company under the name Silicone SF 1188.

This product is prepared according to the method of Example 1.

When applied to the hair after shampooing, this formula provides good wet and dry combing properties and a very good shine to the hair.

EXAMPLE 3

| Rinse Conditioner | |
|---|---|
| Ingredient | % by wt. |
| Water | 81.2 |
| Hydroxyethyl cellulose[1] | 1.0 |
| Quaternium 21 | 3.5 |
| Quaternium 36[7] | 4.0 |
| PVP/VA copolymer (30/70)[8] | 3.0 |
| Ethanol | 7.0 |
| Perfume | 0.2 |
| Formalin | 0.1 |
| | 100.0 |

[7]Stearyl hydroxyethyl di-2-ethoxyethanol ammonium chloride purchased from American Hoechst as 21% dispersion of quaternary salt in water.
[8]Polyvinylpyrrolidone/vinyl acetate copolymer (30/70) purchased from GAF Corporation under the name PVP/VA E-335 as a 50% by weight solution of polymer in ethanol.

This product is prepared according to the method of Example 1. Quaternium 36 is used as a dispersant. Similarly good hair conditioning results are obtained when this product is applied to the hair.

EXAMPLES 4-7

| Ingredient | EX. 4 % by wt. | EX. 5 % by wt. | EX. 6 % by wt. | EX. 7 % by wt. |
|---|---|---|---|---|
| Water | 82.7 | 82.7 | 82.7 | 82.7 |
| Quaternium 6[9] | 6.0 | 6.0 | — | — |
| Quaternium 21[2] | — | — | 6.0 | 6.0 |
| PVP/VA Copolymer (50/50)[5] | 3.0 | — | 3.0 | — |
| PVP/VA Copolymer (30/70)[8] | — | 3.0 | — | 3.0 |
| Ethanol | 7.0 | 7.0 | 7.0 | 7.0 |
| Hydroxyethyl cellulose[1] | 1.0 | 1.0 | 1.0 | 1.0 |
| Perfume | 0.2 | 0.2 | 0.2 | 0.2 |
| Formalin | 0.1 | 0.1 | 0.1 | 0.1 |
| | 100.0 | 100.0 | 100.0 | 100.0 |

[9]Polyoxypropylene (9) methyldiethyl ammonium chloride (98%) and water (2%) purchased from Witco Chemical Corporation as Emcol CC-9.

All of the foregoing products when applied to the hair as rinse conditioners after shampooing provide very good conditioning properties such as slip (spreadability), shine and wet and dry combing properties. The compositions of Examples 6 and 7 which contain the quaternary having the longer propoxylated chain impart superior slip, wet and dry combing, shine and antistatic properties to hair. Also, all of the compositions are stable when aged at 25° C.

EXAMPLE 8

| Hair Conditioning Mousse | |
|---|---|
| Ingredient | % by wt. |
| Water | 81.23 |
| Hydroxyethyl cellulose[1] | 0.27 |
| Quaternium 21 | 0.9 |
| Quaternium 22[3] | 1.1 |
| PVP/VA (70/30) copolymer[4] | 0.9 |
| Ethanol | 5.4 |
| Perfume | 0.2 |
| Propellant Blend | 10.0 |
| 80% isobutane | |
| 20% propane | |
| | 100.0 |

With the exception of the propellant ingredient, the foregoing composition is prepared in accordance with the procedure of Example 1. The resultant mixture in the form of a milky solution is filled into an aerosol container and said container is closed with a valve of the type used on aerosol shaving cream. Thereafter, the valved container is pressurized by adding the propellant compounds thereto. When the valve is activated by the consumer, a quick breaking foam mousse of the low foam type is expelled which provides excellent conditioning effects when distributed throughout the consumer's hair.

EXAMPLE 9

| Hair Conditioning Mousse | |
|---|---|
| Ingredient | % by wt. |
| Water | 68.53 |
| Hydroxyethyl cellulose[1] | 0.27 |
| Quaternium 21 | 0.9 |
| PVP/VA (70/30) copolymer | 0.9 |
| Cocoamidopropyl dimethyl betaine | 0.3 |
| Ethanol | 18.9 |
| Perfume | 0.2 |
| Propellant Blend | 10.0 |
| 80% isobutane | |
| 20% propane | |
| | 100.0 |

This product is prepared and filled into a valved container in accordance with the procedure of Example 8. When sprayed from the container, this product exhibited a delayed breaking foam—a fairly stable, stiff foam—which provided good hair conditioning effects when distributed throughout the hair.

EXAMPLE 10

| Hair Conditioning Mousse | |
|---|---|
| Ingredient | % by wt. |
| Water | 67.58 |
| Hydroxyethyl cellulose[1] | 0.27 |
| Quaternium 21 | 0.45 |
| Stearyl hydroxyethyl, di-2-ethoxyethanol ammonium lactate | 0.8 |
| PVP/VA (70/30) copolymer | 1.35 |
| Ethanol | 19.35 |
| Perfume | 0.20 |
| Propellant Blend | 10.0 |
| 80% isobutane | |
| 20% propane | |
| | 100.0 |

This product is prepared and filled into a valved container in accordance with the procedure of Example 8.

This hair mousse produce foamed well upon discharge from the container—exhibiting a stiff foam—and applied easily to dry hair tress.

The following Tress Tests were performed on the products of Examples 8, 9 and 10, and compared to Alberto Mousse presently on the market, in Table I below. All products are applied to dry hair tresses and the tresses are evaluated for the characteristics listed in Table I.

TABLE I

| Characteristic | Ex. 8 | Ex. 9 | Ex. 10 | Alberto Mousse |
|---|---|---|---|---|
| Nature of application | slippery - easy on application | slippery - easy on application | slippery - easy on application | not too slippery - more difficult to spread throughout hair |
| Ease of wet combing (after application) | excellent | excellent | excellent | fair |
| Hair stiffness (hold) | moderate | light | heavy | heavy |
| Degree of shine | high | moderate | excellent (high) | high |
| Neatness after comb-out | excellent | very good | excellent | good |

Mousse products of Examples 8 and 9 have light to moderate hold properties as compared to the commercial control product. However, compositions 8 and 9 provide better ease of application, easier comb-out and better overall appearance than the control mousse. Slightly less shine properties were found with Example 9 which was probably caused by the presence of the betaine used to produce better foam properties. The product of Example 10 had the best overall conditioning properties including the best foaming and discharge properties.

In Examples 8–10, a $C_3$–$C_4$ hydrocarbon propellant is present as an essential ingredient in proportions of 3% to 20%, preferably 5% to 15%, by weight of the ultimate mousse composition. In the mousse products, the inclusion of the propellant typically reduces the proportion of the other essential ingredients on a pro rata basis because the normal procedure is to admix 80 to 97 parts by weight of the conditioning composition with 3 to 20 parts by weight of propellant in an aerosol container.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

What is claimed is:

1. A hair rinse conditioning composition which imparts superior dry feel and high luster properties to hair treated therewith and is readily removable from the hair by simply shampooing consisting essentially of by weight, a ternary mixture of 0.5% to 15% of a polyvinylpyrrolidone/vinyl acetate (PVP/VA) copolymer, in place of the fatty materials conventionally used, having a weight ratio of PVP/VA varying from 70:30 to 30:70; 0.1% to 10% of a hydrophilic cationic quaternary ammonium salt which corresponds to the following formula:

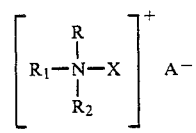

wherein R and $R_1$ each is an alkyl radical containing 1–3 carbon atoms; $R_2$ is a polyoxyalkylene radical represented by either $[CH_2CH(R_4)O]_nH$ or alkylene $O[CH_2CH(R_4)O]_nH$ where $R_4$ is an alkyl radical of 1–2 carbon atoms; n is 3 to 60, and alkylene contains not more than three carbon atoms; X is a lower alkyl or alkenyl radical containing 1 to 4 carbon atoms or is an alkaryl radical containing from 7 to 9 carbon atoms; and A is an anion selected from the group consisting of chlorine, bromine, hydroxy, sulfate, metho- or ethosulfate, nitrate, phosphate, acetate, formate and sulfonate; the weight ratio of said quaternary salt to said copolymer being in the range of 1:5 to 20:1; and 0.1% to 4% of a water soluble nonionic cellulose polymer in 71% to 99.3% of an aqueous medium, said composition having a pH in the range of 3 to 6.

2. The hair rinse composition according to claim 1, wherein the polyoxyalkylene radical is $CH_2CHCH_3O$.

3. The hair rinse composition according to claim 2, wherein the hydrophilic cationic quaternary compound is polyoxypropylene (40) quaternary ammonium chloride.

4. The hair rinse composition according to claim 1, wherein the water soluble nonionic cellulose polymer is hydroxyethyl cellulose.

5. The hair rinse composition according to claim 1 which contains, in addition, from 0.1% to 8% by weight of a hydroxylated quaternary ammonium compound containing polyethoxy radicals, a gluconamidopropyl radical or a hydroxylated gluconamido-$C_1$–$C_3$ alkyl radical attached to the nitrogen atom.

6. The hair rinse composition according to claim 1 wherein said copolymer is present in an amount of 0.9% to 10%, said hydrophilic quaternary compound is present in an amount of 0.45% to 8% by weight, the weight ratio of said quaternary compound to said copolymer is 1:3 to 2:1, said nonionic cellulose polymer is present in an amount of 0.2% to 2% by weight and said aqueous medium is present in an amount of 80% to 98.3% by weight.

7. The hair rinse composition according to claim 1, which is in the form of a pourable opaque or clear liquid having a minimum viscosity of 500 centipoises and a maximum viscosity of about 8000 centipoises.

8. An opaque hair rinse composition according to claim 7 comprising a mixture of polyoxypropylene (40) methyldiethyl ammonium chloride, a polyvinylpyrrolidone/vinyl acetate copolymer in a 70:30 weight ratio of PVP/VA and hydroxyethyl cellulose, in said aqueous medium.

9. The hair rinse composition according to claim 8 which contains, in addition, 0.1% to 8% by weight of gluconamidopropyl dimethyl-2-hydroxyethyl ammonium chloride.

10. The hair rinse composition according to claim 6 wherein said hydrophilic quaternary compound is polyoxypropylene (40) methyldiethyl ammonium chloride, said copolymer is polyvinylpyrrolidone/vinyl acetate in a 50:50 weight of PVP/VA ratio and said cellulose is hydroxyethyl cellulose.

11. The hair rinse composition according to claim 1 which is in the form of a mousse and contains, in addition, from 3% to 20% by weight of a $C_3$–$C_4$ hydrocarbon propellant.

12. The hair rinse composition according to claim 11 wherein said propellant is present in an amount of 5% to 20% by weight.

* * * * *